(12) United States Patent
Hutchins et al.

(10) Patent No.: US 7,107,852 B2
(45) Date of Patent: Sep. 19, 2006

(54) METHOD OF INSPECTING FOOD STUFFS AND/OR ASSOCIATED PACKAGING

(75) Inventors: David Arthur Hutchins, Kenilworth (GB); Duncan Robert Billson, Kenilworth (GB); Tat Hean Gan, Kampung Boyan (MY); David Schindel, Ottawa (CA)

(73) Assignee: University of Warwick, Coventry (GB)

( * ) Notice: Subject to any disclaimer, the term of this patent is extended or adjusted under 35 U.S.C. 154(b) by 0 days.

(21) Appl. No.: 10/505,807

(22) PCT Filed: Feb. 26, 2003

(86) PCT No.: PCT/GB03/00828

§ 371 (c)(1),
(2), (4) Date: Mar. 18, 2005

(87) PCT Pub. No.: WO03/073093

PCT Pub. Date: Sep. 4, 2003

(65) Prior Publication Data

US 2005/0155430 A1 Jul. 21, 2005

(30) Foreign Application Priority Data

Feb. 27, 2002 (GB) .................................. 0204572.2

(51) Int. Cl.
*G01N 29/50* (2006.01)
*G01N 33/02* (2006.01)
*G01N 29/02* (2006.01)
*G01N 29/07* (2006.01)
*G01N 29/11* (2006.01)

(52) U.S. Cl. ............................ 73/598; 73/597; 73/599; 73/600

(58) Field of Classification Search ..................... None
See application file for complete search history.

(56) References Cited

U.S. PATENT DOCUMENTS

| | | | | |
|---|---|---|---|---|
| 3,894,198 A | * | 7/1975 | Murayama et al. | 381/114 |
| 4,208,915 A | * | 6/1980 | Edwards | 73/620 |
| 4,821,573 A | * | 4/1989 | Nagata et al. | 73/597 |
| 4,949,312 A | * | 8/1990 | Iwasawa | 367/7 |
| 5,036,892 A | * | 8/1991 | Stembridge et al. | 141/1 |
| 5,767,407 A | * | 6/1998 | Sinha | 73/579 |
| 5,861,548 A | * | 1/1999 | Melvin et al. | 73/52 |
| 5,929,337 A | * | 7/1999 | Collins et al. | 73/597 |
| 6,186,004 B1 | * | 2/2001 | Kaduchak et al. | 73/596 |
| 6,324,901 B1 | * | 12/2001 | Fluh et al. | 73/61.75 |
| 6,782,752 B1 | * | 8/2004 | Basir et al. | 73/625 |
| 2005/0068535 A1 | * | 3/2005 | Bond et al. | 356/433 |

OTHER PUBLICATIONS

Raffaella Saggin et al., *Non-contact Ultrasonic Measurements in Food Materials*, Food Research International, vol. 34, 2001, pp. 865-870.

* cited by examiner

*Primary Examiner*—Hezron Williams
*Assistant Examiner*—Rose M. Miller
(74) *Attorney, Agent, or Firm*—Workman Nydegger

(57) ABSTRACT

A system to perform measurements on liquids, meat, viscous sugar or starch-based materials, and other foodstuffs using air-coupled ultrasound is provided. The technique uses ultrasonic transducers (advantageously capacitive transducers with polymer membranes), to generate ultrasonic signals in air, and to receive these signals after they have passed through the material under test. An ultrasonic pulse-compression process is then applied to increase the sensitivity of signals transmitted through the materials.

11 Claims, 2 Drawing Sheets

METHOD OF INSPECTING FOOD STUFFS AND/OR ASSOCIATED PACKAGING

FIELD OF THE INVENTION

The invention relates to a method for inspecting foodstuffs and/or associated packaging to detect an irregularity therein or a value of a parameter thereof.

BACKGROUND OF THE INVENTION

The need to test foodstuffs in an industrial context has increased over the last twenty years for a number of reasons. Firstly as the world becomes more litigious, manufacturers need to ensure that no foreign bodies are included in with their products: a single piece of glass could potentially ruin a company.

Secondly, as manufacturers mass-produce their products, there is a need to ensure that the quantity of food within a container is exact. For example an extra 3 cc within each soft-drink bottle over a production run of hundreds of thousands of units per week will cost the manufacturer thousands of pounds, which can be saved by using a more exact on-line measuring system in the packing/bottling plant.

Thirdly, processed meat and fish products such as beefburgers, fish-fingers and 'chicken nuggets' will inevitably contain a small number of bones, as a consequence of the processing not being 100% perfect. This is highly undesirable, as finding a bone in one of these products is unpleasant to the consumer, especially if he or she is a child. This will tarnish the reputation of the manufacturer, and will reduce the repeat-buying of the product. A method of checking for bones in the 'de-boned' product is therefore highly desirable.

Finally, there are an assortment of material properties of the food material that might be desirable to measure. These might include measuring the homogeneity of the material (for example the homogeneity of strawberry jam is determined by the number of strawberries in it), or the velocity profile of the material, which can be used to measure the temperature distribution within a container. It is also desirable to be able to test the characteristics of the packaging material itself, since this could also affect the product shelf-life.

There has been considerable activity in this general area: much research has been carried out on the use of physical measurements to determine the properties of food. This can be to determine the physical properties of the foodstuff (eg. in emulsions, powders and other forms), or to detect foreign objects, surface defects and food contamination. In particular, there has been recent interest in using ultrasound to investigate the content of food products. One reason for this is that any change in the acoustic property of the test medium could then be related to changes in the food product.

Ultrasound has the ability to differentiate between both the propagation velocity within various media, and the differences in acoustic impedance between different regions within a given volume. Thus, using the usual contact or immersion techniques, ultrasound can be used to measure the moisture content of the food products and for liquid level measurement. However, these techniques require a coupling medium between the test sample and the transducer surface and this can be a considerable drawback. In certain cases, the need to use a couplant makes testing difficult, for instance if contamination of the food or container has to be avoided. For these reasons, X-rays have been used to detect anomalies or foreign objects present in food, usually in throughtransmission. This is undesirable for several reasons, including cost and operator-safety concerns. Other techniques such as Magnetic Resonance Imaging (MRI) can be used to study the temperature distribution in food samples, although this is an expensive and complicated method.

SUMMARY OF THE INVENTION

In accordance with the invention there is provided a method of inspecting foodstuffs and/or associated packaging to detect an irregularity in, or a value of a parameter of, said foodstuffs and/or associated packaging, comprising: driving an ultrasonic transmitter with a swept-frequency chirp signal, to produce a transmitter output signal; passing the transmitter output signal through a food item and/or item of associated packaging to be inspected and through any intervening air between said food item and/or item of associated packaging and the transmitter; receiving the emerging signal in an ultrasonic receiver; cross-correlating the received signal with a reference signal corresponding to the driving chirp signal, and detecting from the result of the crosscorrelation step the presence of said irregularity or the value of said parameter.

Such a method can be used for a variety of applications. These may include the detection of variations in consistency within starch or sugar-based (viscous liquid) foodstuffs, the detection of liquid level in polymer-based soft-drink bottles, the detection of foreign objects within foodstuffs (such as bones in fish and meat). Furthermore, the method can be combined with techniques such as tomographic imaging and phased-array imaging to produce images of the material being tested. Testing may be carried out on the packaging containing the foodstuffs in addition to, or in place of, the foodstuffs themselves.

Advantageously, the ultrasonic transmitter and receiver may take the form of a polymer-film capacitive transducer, since this has a broad bandwidth response and can therefore be used to provide images of a wide range of substances and materials.

BRIEF DESCRIPTION OF THE DRAWINGS

Embodiments of the invention will now be described, purely by way of non-limiting example only, with reference to the drawings, in which.

DETAILED DESCRIPTION OF EMBODIMENTS OF THE INVENTION

Figure 1:
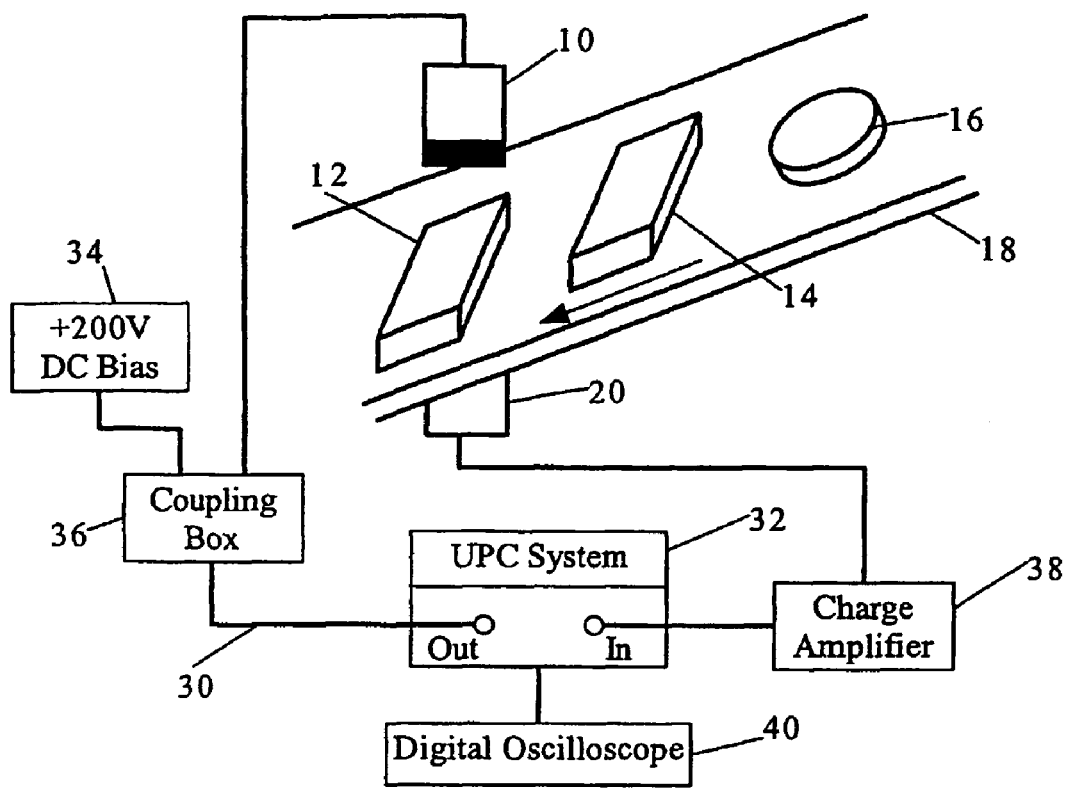
FIG. 1 illustrates an arrangement in accordance with the invention for detecting bones in a fish sample.

There are two basic approaches to the generation and detection of ultrasound in air. The first is to use a piezoelectric transducer system, which has been optimised to work at a chosen centre frequency. Such transducers can be of conventional piezo-ceramic, or constructed from 1–3 connectivity composites. In both cases, a matching layer, or set of layers, are used to match the impedance to air. The result is typically tuned to the resonant frequency for through-transmission of the solid sample in air. This optimises signal levels and allows imaging to take place. The technique, however, can only operate over a range of sample configurations, as the bandwidth has to be carefully controlled.

The present invention employs an alternative technique which is to use capacitance transducers. These have a much wider bandwidth and can be used under wide-bandwidth transient excitation to give images of a range of materials including composites, metals etc. Through-transmitted signals for conventional impulsive excitation give information about the sample, but are of low amplitude, and hence would conventionally require signal averaging to improve the signal-to-noise levels. By contrast, the present invention uses a pulse compression technique to exploit the natural bandwidth of polymer-filmed capacitance devices, and to increase the signal-to-noise ratio to a level where it is suitable for on-line industrial testing. This technique uses a swept-frequency 'chirp' signal, which is used to provide a broad-bandwidth transient, which can be detected and processed in air using a cross-correlation technique. This approach greatly improves the signal-to-noise ratio, while simultaneously giving excellent time resolution. A chirp signal can be represented as $$C(t)=H(t)\cdot\sin(\omega_s t+\pi Bt^2/T) \quad 0<t<T \quad (1)$$

Where $\omega_s$ is the starting angular frequency;
B is the bandwidth of the signal;
T is the duration of the pulse.
H(t) is a Hanning filter function.

The Hanning filter is important to ensure good sensitivity, and helps to reduce the amount of side lobes in the signal.

In order to produce the compressed pulse signal, P(t), the received low amplitude signal $C_T(t)$ from any experiment is band-pass filtered within the chirp bandwidth to reduce noise levels. The waveform is then cross-correlated with the reference signal C(t):

$$P(t)=C(t)*[C_T(t)] \quad (2)$$

The compressed pulse, P(t), is thus produced by the correlation of the received signal $C_T(t)$ with the original reference signal, C(t). The correlated result is in the form of a time signal, the position of which represents the position in time of the transmitted signal. Signal-to-noise ratios are greatly improved with respect to a conventional through-transmitted transient signal. The pulse compression output can be interpreted much like a conventional ultrasonic waveform, in that the amplitude of the compressed pulse as a function of time is related to the amplitude of the received chirp waveforms as a function of time. |P(t)| also contains information concerning the material through which the signal has travelled.

There are thus three primary benefits of this pulse-compression technique as applied to air-coupled measurements of foodstuffs. Firstly, the accuracy of time-of-flight measurements will be improved when using pulse-compressed techniques Secondly, such a coded waveform has the advantage that it can be detected when the received chirp level is well below the noise floor of the detector (i.e. since the noise is random and thus un-correlated with the chirp shape). Finally, high ultrasonic energy levels can be transferred into a material due to the use of a chirp signal, to give a good signal-to-noise ratio (SNR).

In order that the invention may be more fully understood, two specific realisations of an ultrasonic test method for the testing of foodstuffs in accordance with this invention will now be described, by way of example. The first realisation concerns the detection of fish bones and is illustrated in FIGS. 1 and 2.

The apparatus shown in FIG. 1 includes a capacitive ultrasonic transmitter 10, which is directed towards an item of food 12 placed, along with other such items, 14, 16 on a conveyor belt 18 and positioned by movement of the belt to be directly underneath the transmitter 1. Underneath the belt 18 is a capacitive receiver 20, which is essentially of the same design as the transmitter 10 and receives ultrasonic energy from the transmitter after it has traversed the thickness of the food item 12.

Figure 2:
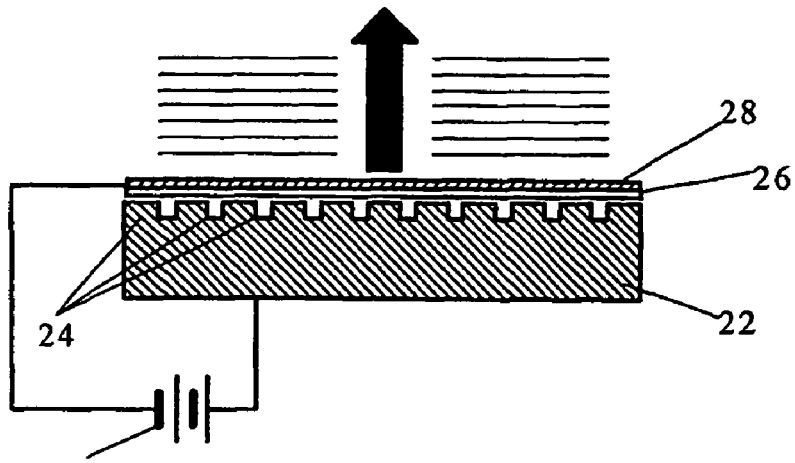
FIG. 2 is a sectional diagram of a capacitive transducer.

The form of the transmitter 10 and receiver 20 is shown in FIG. 2. In FIG. 2 the ultrasonic transducer, which is known per se in the literature, comprises a micromachined silicon backplate 22, which contains arrays of small cylindrical holes 24. These holes act as air springs underneath a membrane 26, which takes the form of a metallised polymer film and has on an outer surface thereof a conducting electrode 28. The backplate is coated with gold to make it conducting, while the outer electrode 28 of the membrane is grounded.

As already stated, this type of transducer can be used either as a source or as a detector. As a source, a transient driving voltage 30 is applied from an ultrasonic pulse compression unit 32 together with an optional dc bias voltage 34, the two voltages being combined in a coupling box 36. As a receiver, the bias voltage is required to give charge variations when the membrane moves, these charge variations being picked up in a charge amplifier 38 (FIG. 1). The transducers in the present system have an active aperture of 10 mm diameter, and are fitted into a fully shielded metallic case.

The arrangement of FIG. 1 is used to detect a bone in a fish fillet 12. The transmitted signal will change when a bone is present in the area under test (due to ultrasonic reflections at the bone/flesh interface) this change being displayed in, eg., an oscilloscope 40. This can trigger an alarm, indicating the presence of a bone. For practical testing of foodstuffs in an industrial environment (on a production line), multiple sources and/or receivers may be necessary to ensure that an adequate width of test is covered.

Figure 3:
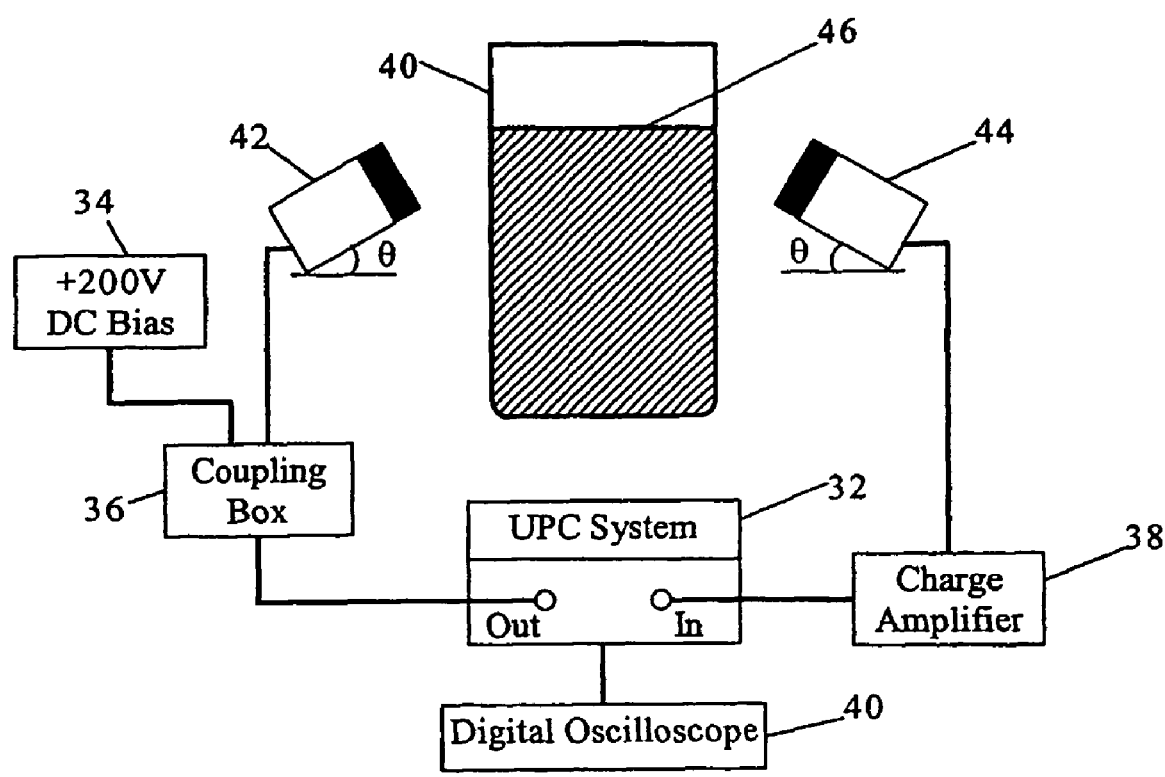
FIG. 3 shows the use of the method of the present invention for detecting the level of a liquid.

A second use of the method according to the invention is shown in FIG. 3. In this arrangement the height of liquid within a container 40 is accurately measured and since the container's dimensions are known, the volume of liquid can also be accurately determined.

In this arrangement, a pair of transducers 42, 44 are aimed at the nominal surface level 46 of liquid in a container, (eg. a soft drink in a bottle), the angle of inclination of the transducer being an angle θ suitable to achieve this. The ultrasonic beam from the transmitter 42 is slightly fanned out and covers a given width at the liquid surface, being then reflected off of the underside of the liquid surface 46 and impinging on the receiver 44. A variation of the liquid level within the container causes the time of arrival of the ultrasound at the receiver 44 to vary accordingly, this time of arrival being measured and the liquid volume calculated accordingly. It should be noted that the variation in liquid level is not anticipated to be great, so that angle θ can remain constant during measurement. The arrangement and operation of the electronic apparatus is the same as for the first example.

It can be seen that this technique is:
a) non-contacting
b) relatively inexpensive to install and operate
c) intrinsically operator safe
d) non-invasive (i.e. it does not affect the sample under test)
e) suitable for installation on a production line In summary, then, a new air-coupled (non-contacting) ultrasonic technique has been developed, which can be used to measure properties of food which are of interest to the food manufacturing/processing industry. This incorporates two (or more) ultrasonic transducers, which are advantageously broadband capacitive types, together with a pulse-compression signal-processing technique. The combination shows good signal-to-noise ratio for ultrasonic through-transmission, is suitable for incorporation onto a production line, and can be used to measure a variety of parameters, including the level of liquid within a container, either by monitoring the amplitude of through-transmission, or by using a reflection from the water surface.

The technique can also be used to detect the presence of foreign objects within foodstuffs, bones in fish or meat, and other parameters, such as temperature profiles or food homogeneity. It can also be applied to foodstuffs in containers, to containers alone and to foodstuffs where no container is used. It can be combined with other techniques, such as tomographic reconstruction and phased-array scanning, to generate images of the foodstuffs being tested, using single transducers, multiple transducers, or transducer arrays.

The invention claimed is:

1. Method of inspecting foodstuffs and/or associated packaging to detect an irregularity in, or a value of a parameter of, said foodstuffs and/or associated packaging, comprising:
    driving a capacitive ultrasonic transmitter with a swept-frequency chirp signal to produce a transmitter output signal;
    air-coupling the transmitter to a food item and/or item of associated packaging;
    passing the transmitter output signal through a food item and/or item of associated packaging to be inspected and any intervening air between said food item and/or item of associated packaging and the transmitter;
    receiving the emerging signal in an ultrasonic capacitive receiver;
    cross-correlating the received signal with a reference signal corresponding to the driving chirp signal; and
    detecting from the result of the cross-correlation step the presence of said irregularity or the value of said parameter.

2. Method according to claim 1, wherein the irregularity is a foreign body in said food item.

3. Method according to claim 1, wherein the food item is a liquid and the emerging signal is the transmitter output signal as reflected from a surface of the liquid, the detection step detecting the position of said surface.

4. Method according to claim 1, wherein a capacitance transducer having a polymer-film membrane is used as the transmitter and receiver.

5. Method according to claim 2, wherein a capacitance transducer having a polymer-film membrane is used as the transmitter and receiver.

6. Method according to claim 3, wherein a capacitance transducer having a polymer-film membrane is used as the transmitter and receiver.

7. Method according to claim 1, wherein said swept-frequency chirp signal provides a broad-bandwidth transient.

8. Method according to claim 1, wherein the step of cross-correlating comprises using pulse compression of signals.

9. Apparatus for inspecting foodstuffs and/or associated packaging to detect an irregularity in, or a value of a parameter of, said foodstuffs and/or associated packaging, comprising:
    an ultrasonic capacitive transmitter and an ultrasonic capacitive receiver;
    a supporting surface for supporting a food item and/or item of associated packaging, the supporting surface being positioned between the ultrasonic transmitter and receiver and the ultrasonic transmitter and receiver each being orientated such as to face said food item and/or item of associated packaging;
    an air space between the transmitter and said food item and/or said item of associated packaging; whereby air coupled ultrasonic transmission is achieved;
    a chirp signal source for driving the ultrasonic transmitter;
    an amplifier for amplifying a signal received by the ultrasonic receiver; and
    a processing means connected to the amplifier and comprising a source of a reference signal corresponding to said driving chirp signal and a cross-correlating means for cross-correlating the reference signal and the amplified received signal, an output of the cross-correlating means providing, in use, an indication of the presence of said irregularity or the value of said parameter.

10. Apparatus according to claim 9, wherein the ultrasonic transmitter and receiver are a polymer-film capacitive ultrasonic transducer.

11. Apparatus according to claim 10, wherein said output of the correlating means provides transient time signals.

* * * * *

UNITED STATES PATENT AND TRADEMARK OFFICE
CERTIFICATE OF CORRECTION

PATENT NO. : 7,107,852 B2  Page 1 of 1
APPLICATION NO. : 10/505807
DATED : September 19, 2006
INVENTOR(S) : Hutchins et al.

It is certified that error appears in the above-identified patent and that said Letters Patent is hereby corrected as shown below:

Column 1
Line 14, change "Firstly" to --Firstly,--
Line 20, change "For example" to --For example,--

Column 3
Line 53, after "techniques" add --.--

Column 4
Line 3, change "1" to --10--

Signed and Sealed this

Twenty-fifth Day of December, 2007

JON W. DUDAS
*Director of the United States Patent and Trademark Office*